US008520925B2

(12) United States Patent
Duret

(10) Patent No.: US 8,520,925 B2
(45) Date of Patent: Aug. 27, 2013

(54) DEVICE FOR TAKING THREE-DIMENSIONAL AND TEMPORAL OPTICAL IMPRINTS IN COLOR

(76) Inventor: François Duret, Fleury D'aude (FR)

( * ) Notice: Subject to any disclaimer, the term of this patent is extended or adjusted under 35 U.S.C. 154(b) by 0 days.

(21) Appl. No.: 13/702,753

(22) PCT Filed: Jun. 8, 2011

(86) PCT No.: PCT/FR2011/051300
§ 371 (c)(1),
(2), (4) Date: Dec. 7, 2012

(87) PCT Pub. No.: WO2011/154656
PCT Pub. Date: Dec. 15, 2011

(65) Prior Publication Data
US 2013/0108981 A1  May 2, 2013

(30) Foreign Application Priority Data
Jun. 8, 2010  (FR) ...................................... 10 54483

(51) Int. Cl.
*G06K 9/00* (2006.01)
(52) U.S. Cl.
USPC ............... 382/128; 382/100; 433/25; 433/27; 433/29; 433/215
(58) Field of Classification Search
USPC ..................... 382/100, 128; 433/25, 27, 215, 433/30, 15, 29, 72, 75, 76; 600/589, 590; 378/38, 98, 191
See application file for complete search history.

(56) References Cited

U.S. PATENT DOCUMENTS

| | | | |
|---|---|---|---|
| 2002/0028418 A1* | 3/2002 | Farag et al. ...................... | 433/29 |
| 2008/0280260 A1* | 11/2008 | Belikov et al. ................ | 433/215 |
| 2009/0087050 A1* | 4/2009 | Gandyra ........................ | 382/128 |
| 2009/0227875 A1 | 9/2009 | Cao et al. | |
| 2009/0259098 A1 | 10/2009 | Krattiger | |
| 2010/0316973 A1* | 12/2010 | Remmers et al. ............. | 433/214 |

FOREIGN PATENT DOCUMENTS
EP  2 166 303 A1  3/2010

* cited by examiner

*Primary Examiner* — Ali Bayat
(74) *Attorney, Agent, or Firm* — Andrew W. Chu; Craft Chu PLLC

(57) ABSTRACT

Device for taking three-dimensional and temporal optical imprints in color, including a three-dimensional dental imaging device that does not employ structured light projection. The device includes a stereo camera having at least two CCD or CMOS color sensors in preset positions, an optical system of fixed and preset focal length, an LED lighting system, and an electronic system located behind or near the sensor, controlling the latter but also the LEDs illuminating the imprint capture region. The system includes a central processing unit and a card for controlling said LEDs. The sensors are distributed over all or part of a dental arch, being placed in a sort of optical impression tray allowing a complete image of the arch to be captured in a single exposure.

10 Claims, 7 Drawing Sheets

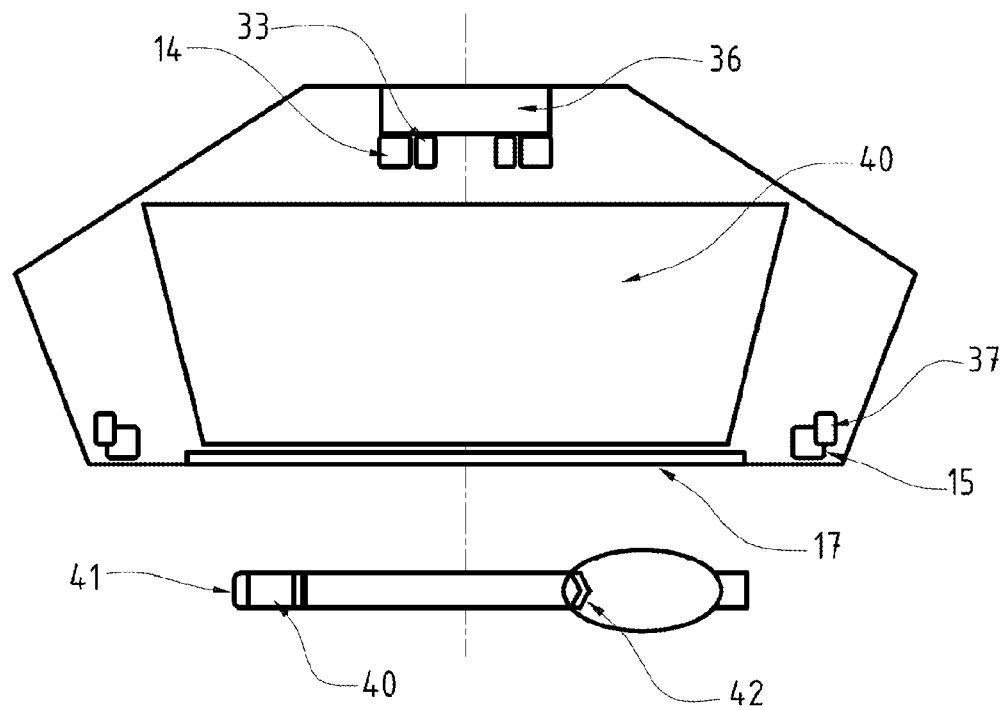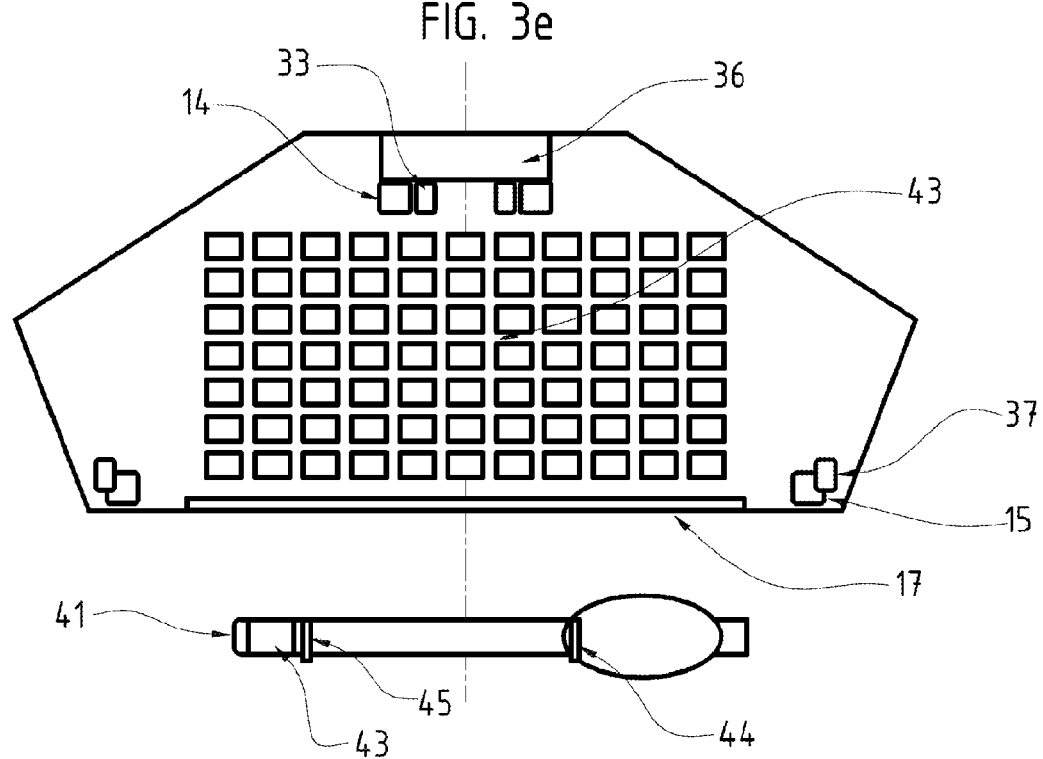

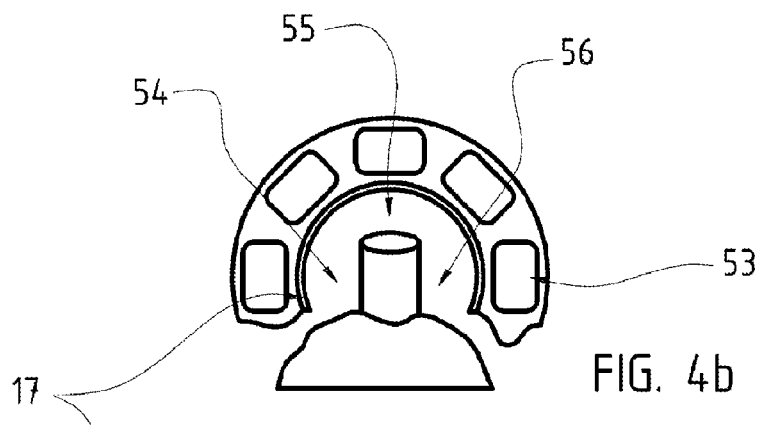
FIG. 4b
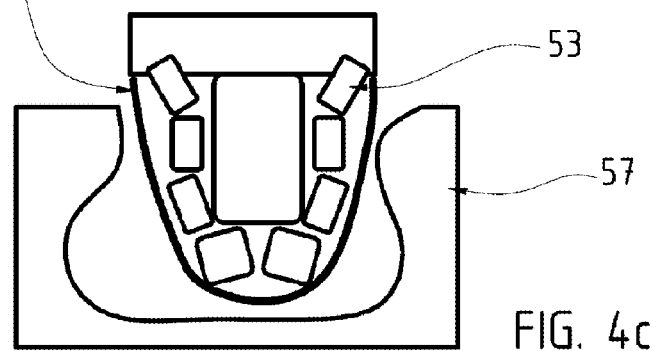
FIG. 4c
FIG. 5a
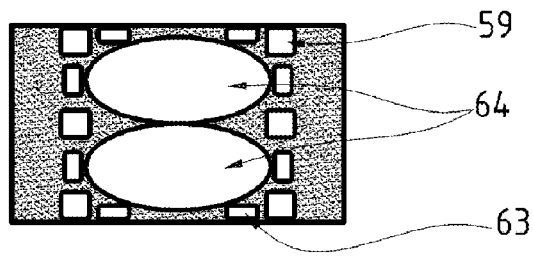
FIG. 5b
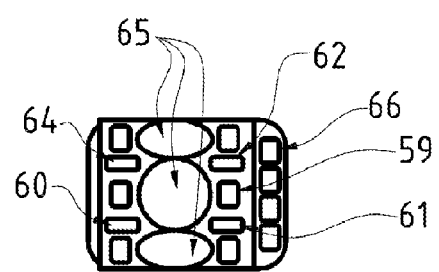
FIG. 5c
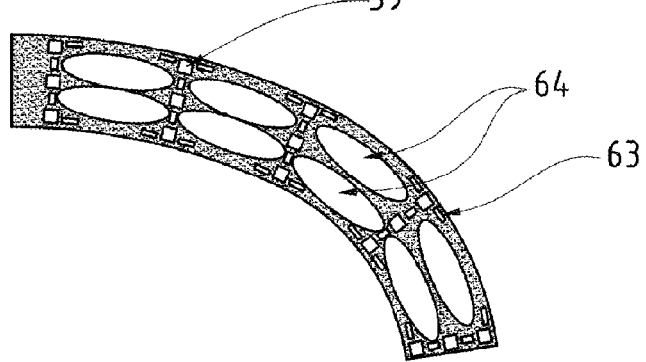

DEVICE FOR TAKING THREE-DIMENSIONAL AND TEMPORAL OPTICAL IMPRINTS IN COLOR

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a novel device for taking a three-dimensional and temporal optical imprint in color of a volume of a few cubic centimeters at the surface of the human body, ensuring its structural integrity, applicable in the dental field for taking intraoral pictures, but also ensuring in this field, an assistance for diagnostic, including a miniaturized stereo system associated with one or several electronic CCD or CMOS color sensors for a specific and modulated lighting with LEDs of one or several wavelengths permitting to measure specular or Lambertian uniform surfaces without deposit of a "coating" on the surface of the teeth or gums, a central analog-digital data control and conversion unit, but also and eventually color and movement analysis software for assisting diagnostics by reflection, global or selective penetration of the light radiation of judiciously selected LEDs into the lighting used, without requiring the slightest mechanical, optical or electro-optical scanning.

2. Description of Related Art Including Information Disclosed Under 37 CFR 1.97 and 37 CFR 1.98.

The taking of imprints by optical means in order to perform diagnostics or make prostheses was described for the first time in 1973 by the applicant in his graduate thesis (DDS) under the title "Optical imprint". The applicant has made numerous publications on this matter. He namely filed the first patent dealing with the interference for taking intraoral optical imprints in U.S. Pat. No. 4,663,720 and U.S. Pat. No. 4,742,464, and also in U.S. Pat. No. 4,611,288, but also in U.S. Pat. No. 5,092,022. The applicant also proposed the taking of optical imprints in dentistry and medicine through projecting masks, FR 84.05173), scanning in profilometric phase in conical projection, U.S. Pat. No. 4,952,149, or through dynamic monitoring by means of LEDs, WO 94/00074.

Since 1982 many papers deal with the taking of optical imprints through scanning in profilometric phase in parallel projection, the modeling or machining of the prosthesis.

All these works and inventions have led to many embodiments and more than twenty commercially available systems.

Since 2000, different solutions have been proposed, not in the mouth, but on plaster models made from imprints made in the mouth using traditional methods, for example in U.S. Pat. No. 7,399,181, or on models built by stereo-lithography, U.S. Pat. No. 10,726,257. This solution has also been proposed in addition to the systems for dentists with a scanning on a model by projection of dots or frames, U.S. Pat. No. 7,335,876.

In the field of orthodontics other proposals have been made to use the optical imprint, as shown in U.S. Pat. No. 7,361,018. These systems have i.e. permitted the commercial development of the system described in U.S. Pat. No. 7,361,017, U.S. Pat. No. 7,393,208, or U.S. Pat. No. 6,318,994, U.S. Pat. No. 6,802,713, U.S. Pat. No. 11,405,972.

As can be seen, among all these systems, few are transposable to the mouth for the following reasons:
- the scanning is too slow, the scanning passes from 2 minutes per tooth to 2 seconds for the fastest ones,
- the apparatus requires having a camera in constant position with respect to the object, which would require to fix the camera, and the patient's head, and
- the displacement mechanism remains complex and inaccurate.

In addition to these drawbacks, all the so-called laboratory systems, which scan a model, lead the dentist to perform a traditional imprint, which does not eliminate the discomfort for the patient and the inaccuracy of the intraoral molding and requires the practitioner to send the part to the laboratory. In addition to this drawback, the technician, when molding the imprint, will add further errors, which considerably affect the accuracy of the optical imprint on which he will work with his computer-assisted design software (CAM) after scanning.

Nowadays, the systems operating in the mouth are presently very few. All these systems use mechanical, optical or electro-optical scanning to perform the measurement of the surface under examination. These methods can be classified into three types, one using the profilometry of the phases in parallel projection in visible or blue light, with conical projection, by scanning of red or infrared fringes in about one hundred milliseconds, and finally, recently the system described in U.S. Pat. No. 7,372,642.

Nevertheless, all these intraoral cameras, the one developed by the present applicant included, have several particularly prohibitory drawbacks:
- these systems are complex to be implemented and require much care in calibration;
- the electronics remains complex, which makes it difficult to reduce the price and makes the camera fragile;
- the cost of the camera is particularly high and can exceed € 30,000; and
- the cameras are generally bulky and heavy, which hinders the user.

In fact, a closer analysis shows that these cameras have several very important drawbacks, in the very principle of the methods used. These drawbacks are unavoidable, because they are related to the choice of these methods.
- a) All these systems, whether in the mouth, on the skin or in the laboratory (on a model), whether they use the OCT (Optical Coherence Tomography) in dermatology or ophthalmology, use the scanning of the surface by mechanical, optical or electro-optical means. Although this scanning of fringes or frames is very fast, it nevertheless requires a movement in the camera itself, which movement can cause blurs or parasitic displacements, which often lead to the rejection of part of the pictures.
- b) this scanning significantly limits the field depth already significantly reduced in a macroscopic picture (of a few cubic centimeters).
- c) the dots of the surface of the object are not measured, but instead the deformation of a light projection on the surface of this object is measured. This first feature requires the developers to cover the teeth with a white layer, referred to as "coating", which degrades in principle the actual measurement of the object. This is indeed often expressed as both an inaccuracy and an inconvenience in the use of the cameras in the mouth.

d) this has obliged the manufacturers to use radiation making the tooth "opaque", as with blue or ultraviolet rays. This is why the present applicant proposed a device using an argon laser. This can be restrictive for the user, even dangerous for the patient.

e) moreover, not measuring the object, but the distortion of the projected light, either a dot, a line, a frame or a phase of this light, eliminates all possibilities of having a perfect match between the color, the shade of the object and its measurement. The only shade that we can have is the color of the projected light.

f) passing from 3D reading to 2D reading in color, when it is used for diagnostics, is completely impossible in dentistry, because only a monochromatic image representing the light of the fringes is recovered.

g) finally, the analysis techniques by profilometry or scanning require to take several pictures of the same spot in order to be capable of extracting the third dimension. This results into a risk of distortion of the data between the first and the last picture, which leads to large errors in correlation and accuracy. The "movement" has always been the enemy of this type of technology.

Finally, though it is possible to measure a tooth, the projected light is still measured, and not the object itself, and this measurement requires to use movements of the source or optics during the reading. As stated above, all these systems are based on the measurement of the distortion of the light displaced and viewed by the camera.

It should be noted that the same also applies in the field of dermatology or ophthalmology. The methods used in 3D reading are recent, expensive and complex, as the OCT apparatus show. That is why these disciplines mainly use 2D measurements, which are less burdensome for anatomical subcutaneous studies or their expansions to the (eventual) pathology.

The techniques used nowadays are the following:

a) videodermatoscope, which consists of a currently widely used basic tool, permitting to have an amplified image of the skin (up to 70×). The digital technology allows taking digital photographs as well as records, which thus facilitates the comparison over time and the sharing of information between clinicians. The devices offer on the other hand ancillary functionalities, such as the possibility of using light sources of different wavelengths for illuminating the skin, or also image processing such as the automatic segmentation of the lesions or also the automatic extraction of ABCD criteria.

The cost of such a device remains however high, and no clinical study seeking to show an improvement in the diagnosis compared to the simple clinical examination has been found. Moreover, the videodermatoscope does not provide information in depth.

b) echography, which allows in-depth exploration of the lesions. With frequencies in the range from 10 to 50 MHz, it is possible to go down to 12 mm with an axial resolution of 150 microns. This technique is used for the study of the subcutaneous extension in pre-operative analysis and the search for metastatic melanoma, where it has shown excellent capabilities in terms of sensitivity and specificity. However, the proper use of such a device requires, however, to acquire some experience in reading ultrasound images; on the other hand, it is much more difficult to add informative post-processing on these images, unlike with the multispectral techniques (see below).

c) the OCT, which is based on interferometric optical techniques, allowing imaging the skin in depth in 3D with good lateral resolution (in the range of 15 μm), higher than that of the echographs. It allows, on the other hand, to carry out imaging almost in real time, but is limited in depth (maximum 1.5-2 mm). Only one device is currently marketed, and the study of its efficiency in the diagnosis of melanoma is currently under study. Though it has a very good resolution in real-time imaging, it operated on a small depth, has no clinical data, operated in cross-section, is difficult to implement and is very expensive.

d) confocal microscopy, which provides 3D images of the epidermis and papillary dermis with very high resolution (1-2 μm lateral resolution, 3-5 μm axial resolution). Its main drawback is that it is very limited in depth (200-500 μm).

These devices have the advantage of having an excellent resolution, a very good melanoma/nevus discrimination (better than the clinical examination alone). But, apart from being of a very high cost, they have a very small depth of analysis.

e) multispectral imaging, which is the technique that has the highest interest today because of the simplicity of the method and its good price/quality ratio. It is indeed a simple imaging technique: it assumes that the skin is organized in layers, and that each layer includes different proportions of substances referred to as chromophores, which have each a relatively characteristic light-absorption spectrum. The main chromophores of the skin are melanin, collagen and hemoglobin, one understands the importance of this method in the study of melanoma, where the proportion of melanin will be changed over a more or less large number of layers. In order to obtain quantitative spatial information on these chromophores, different monochromatic lights (typically ten) are projected onto the skin, and the light re-emitted by the cutaneous skin is measured for each wavelength. One thus obtains information in depth, on which automatic processing can be applied, namely segmenting the lesions, obtaining the ABCD criteria in depth of same and quantifying their proportion of chromophores. However, only depths in the range of 2.5 mm can be reached. The main advantages of the devices are their technique, which is easy to be implemented, the many automatic processing operations that are possible and their good melanoma/nevus discrimination (better than the clinical examination alone). They have the disadvantages of operating only in 2D, of still being expensive, and of operating on a rather limited depth.

There are of course methods under study for skin pathologies using the principles of IRM, PET—scan, of two-photon imaging or of terahertz imaging, but their implementation will be long and it will lead to devices too expensive to be used in private medical offices, which remains the goal to be reached.

Finally, there were some stereographic measurement tests in medicine using two or more than two sensors, which, through the triangular position method, permit to find the third dimension. The use of two sensors permits a stereo vision in well-defined objects, but the methods of mathematical correlations are complex and expensive because the objects used as references are difficult to be identified. The manual action is almost always necessary and the tests performed on teeth proved unusable in the aimed distances and field depths.

Likewise, the development of the images referred to as "triplet imaging system" (L configuration) using cameras placed in an equilateral triangular position position provided valuable information for determining the third dimension by simplifying the triangular position, but the results proved unusable in the dental conditions outlined above. Indeed, all the systems used require knowing the displacement of the camera or of the object between two (or n) acquisitions.

All these drawbacks have led to provide an inexpensive universal solution meeting the criticisms made above.

SUMMARY OF THE INVENTION

The aim of the present invention is to solve the aforementioned drawbacks by providing a complete intraoral reading unit combining very fast, even instantaneous dynamic 3D reading, color display, analysis of the near subcutaneous region and possibility of switching over in real time to 2D display, the whole leading to a very accurate digitizing without addition of "coating".

Thus, the three-dimensional and temporal measuring device through optical color imprint usable in the dental field according to the invention is essentially characterized in that it consists of a device for taking three-dimensional dental pictures that does not use structured light projection, and including to this end:

- a stereo camera comprised of at least two CCD or CMOS color sensors in a predetermined position defining, because of their resetting speed, the reading speed, thus the speed of taking successive imprints, and permitting a static or dynamic reading,
- an optical system of fixed and preset focal length permitting to transmit to said sensors, without distortion, the data displayed on the operating field,
- a LED lighting system for illuminating the area of taking an imprint,
- an electronic system located behind or proximate each of said sensors, ensuring the control thereof, but also that of the LEDs illuminating the area of taking an imprint, and in that said electronic system includes:
- a central control unit capable of collecting, storing and organizing the data captured by said sensors,
- a card for controlling said LEDs, depending on said central unit, and in that said sensors are distributed over the whole or part of a dental arch in order to make an imprint in one single exposure, avoiding the clinical scanning of the arch of the patient by the operator, they are arranged in a kind of optical imprint tray permitting to capture the complete arch in one single exposure.

The optical system can be an endoscope when the sensors are placed outside the reading area, or a simple lens system when the sensors are placed against the reading area. The system can thus be very simple, which is completely impossible in the so-called techniques with structured light, in which it is necessary to have a conduit for the projected light and another one for the reflected image.

The central control unit is eventually also capable of converting the data from analog values into digital values. The fact of not having to control a system for projecting masks or fringes significantly reduces the central unit to a bare minimum: the control of a color stereo dual-picture camera.

The control card is capable of activating preferably a particular LED depending on the implemented programs. Indeed, the LEDs will be controlled alternately or together, or in a varying order depending on the implemented program.

The electronic system also includes:
- a standard supply card capable of operating on USB or on battery. Depending on whether a free system (without wired connection) or a wired system is used, the supply unit remains light, taking into consideration the low power consumption by the implemented components. The camera is thus the first one that can have a wireless connection,
- a miniaturized memory card included in the camera, permitting to store the pictures and to transfer them to the computer using a transportable medium without the need for a USB connection.

The lighting system is a lighting system with LEDs of different wavelengths or colors the mix of which can lead, for example, to white or "day" light, in order to have a real or stimulated (fluorescence) color display. The judicious choice of the LEDs will permit:
- either to display the measured area in daylight (so-called "white" LED)
- or, by activating the LEDs, to highlight determined tissues, such as the mineralized tissues in blue or UV, a fluorescent dental tissue, thus having a particularly "mat" aspect
- or also to display determined "dermal" pathologies, depending on the selected wavelengths. In particular, it is known that the penetrations of wavelengths can be correlated with determined pathologies, the judicious choice of the scanning of the area will permit to display what is not visible to the eye, and this in relief.
- or to permit to identify correlation control points characterized by the marking color used on the measured surface.

This same application also permits to penetrate into rather thin gum areas, as is known in the dental sulcus, providing the operator with a view of the emergence of the tooth. Likewise, a color, e.g. within the reds, permits to avoid adverse salivary effects, unlike with the current methods.

The device also includes a standard, portable, carried or desktop computer containing program and data control and processing software, which is capable of reproducing the information in a 2D or 3D form visible on the screen, but also of addressing the measurements to more or less remote centers (internet, Wifi, Ethernet . . . ), in a form similar to any standard CADCAM system (STL . . . ) or in a specific form, by means of language translation software. In this computer will be placed, before having a miniaturized computing unit, the 3D reproduction and camera control software.

The present invention thus relates to a miniaturized and dynamic stereo color reading device for a small portion of the body associated with an n CCD or n Cmos camera, with an analog digital conversion system, with a central data control unit, with a standard or specific information output, with an amplification of the message received using LEDs of white color or specially designated spectral values, and a wave connection (e.g. WiFi) or a self-powered USB port, and battery-powered or by an electrical connection.

This invention permits to solve the problems outlined above by providing a scalable, inexpensive solution usable in all dental offices, but also as a hand-held instrument in dental prosthesis laboratories, in a simplified form pleasant for the patient.

In particular, this invention solves the many problems evoked above:
1) thanks to the implemented means, the device is simple to be manufactured, which makes it particularly strong,
2) this simplicity has an essential consequence on the manufacturing cost, thus on the sale price, in particular since the democratization of the electronic components used, such as CCDs, CMOS or LEDs, 3) the power-supply unit, which is particularly simple, may be contained in the USB connection permitting to connect to all types of computers capable of receiving the standard output language, such as STL,
4) the manipulation of stereo images, the basis of this new invention, allows self-calibration, eliminating any adjustment in time, which is not the case with the current methods using the so-called structured lights,
5) its operation with CCD or CMOS sensors in a predetermined, immutable spatial position fixed during manufacture with respect to each other, avoids the need of knowing the movements of the object or the cameras (with respect to each other), reducing the problem of disparity to a simple problem of density correlation in the scatter diagram,
6) not using measurements of structured light distortion permits to work on images of the body itself in color,
7) having color images permits to manually or automatically selectively select portions of the human body, for example to identify the teeth and gums separately,
8) operating without structured light also permits not to use "coating" surfaces, known factor of inaccuracy when approaching values close to the micron, which is necessary in all measurements for adjusting a prosthesis or for a diagnosis,
9) using a light-emitting diode permits to display determined slightly subcutaneous or sub-gingival areas, in order to improve the reading in invisible areas without resorting to surgical methods (gingival retractions) or more complex methods (OCT) for simple diagnoses,
10) it also permits, by simple voluntary markings in color, to more easily identify determined naturally colored areas on which one can rely, or to facilitate the correlations of pictures by selecting the lighting of a LED of a color complementary to the marking,
11) with the recent software tools, the autocorrelation is nowadays facilitated by the color information, and permits to dynamically record: a complex surface (complete arch), the movements of these surfaces (upper arches with respect to lower arches),
12) using only one of the image sensors permits to switch from a 3D image to a 2D image, in order to have, with the same tool, a planar analysis and a spatial analysis, which is the basis of many devices nowadays available on the market,
13) one double or triple picture at the same time is enough to extract the third dimension, which avoids any "movement" while capturing the data,
14) the 3D display on the screen is made possible on standard 3D high-definition screens, which is not the case without complex processing with the current intraoral systems,
15) the simplicity of the processing operations permits the use of a low-end standard computer,
16) finally, the proposed apparatus is universal in its field of application, and meets numerous requests in terms of cost, accuracy and diagnostic imaging.

The device of the invention permits to have a dynamic picture by moving over the analysis area, unlike with the systems in profilometric phase, which must take a minimum of four pictures to extract the relief; the system used in this invention merely requires one double picture, which avoids any movement, since the integration of the information at the sensor is immediate.

The present invention thus consists in making a dental imprint using a set of CCD or CMOS sensors in a predetermined position in the geometrical arrangement of the optical system associated with the hardware (control cards) and software (data control software) data control electronics, in order to solve the problem inherent to the conventional stereo systems (knowledge of the varying position of the cameras with respect to each other).

The present invention also consists in compulsorily associating a lighting system with LEDs of a predetermined wavelength, in order to permit in a particularly easy way a putting into correlation of the static or dynamic pictures at the level of the identification of the reference points and the correlation points.

According to a first embodiment, the device includes three sensors intended to be positioned uniformly, according to a known geometry, around the object to be studied, fixed focusing lenses positioned in front of each sensor according to a central optical axis, the position and the spatial orientation with respect to each other of which are perfectly known, said lenses in co-linear position with respect to the viewing axis of the sensor forming three image paths, one for each sensor.

In order to simplify the correlation of the pictures and to adjust the zoom effect between each sensor, the images are captured at the same time, which means that the three 2D images captured at different angular positions arrive at the same time in the image processing system. There is no "time out" between each of these picture takings, which has the advantage of considerably simplifying the image processing and the search for the third dimension. This has the advantage of re-adjusting the scatter diagram that appeared on an area seen by several sensors and of correcting the zoom effect that necessarily appears as a result of the varying position of the object with respect to all the sensors.

The calculation of the third dimension being based on the search for similar dots, which is facilitated by the predefined positioning of the sensors, but particularly difficult for uniform surfaces as the tooth surfaces, is associated with these three sensors of the LEDs in the white range in order to reveal the actual color of the object being measured. The image dots thus contain two additional pieces of information, the time (time of the taking of pictures, which will become common for the three pictures, in order to simplify the calculations) and, without this being mandatory, a fifth dimension that is in turn divisible into a chromatic system, and which corresponds to the color information.

Advantageously, these LEDs can also be of a predetermined wavelength (of a few nanometers) permitting to highlight natural markings (groove bottoms or color areas differentiating tumors, gums or shades of the teeth) or overmarkings made before taking the imprint, made with markers of a complementary color.

Advantageously, these markings may be objects of different shapes placed (in the area being measured), glued or accommodated (in the interdental spaces or on the implant heads) on the object being analyzed.

Advantageously, this or these LEDs are placed around each image-focusing lens placed in front the sensor.

Advantageously, these LEDs can be an association between the white LEDs of a predetermined wavelength, so that the measurements are made from natural and not from artificial colors.

Advantageously, in order to facilitate the search for the third dimension and to reduce the calculations to a single-dimensional geometry, the present invention preferably uses sensors in an equilateral position.

According to a second embodiment, the device according to the invention includes two sensors positioned uniformly around the object being studied, in a known geometry. The focusing lenses are placed in front of each sensor according to a central optical axis, the position and spatial orientation with respect to each other of which are perfectly known. These lenses, in a position co-linear with respect to the viewing axis of the sensor, form two image paths, one for each sensor.

In order to simplify the correlation of the pictures and to adjust the zoom effect between each sensor, the image captures are made at the same time, which means that the two 2D images captured at different angular positions arrive at the same time in the image processing system. There is no "time out" between each of these picture takings, which has the advantage of considerably simplifying the image processing and the search for the third dimension. This has the advantage of re-adjusting the scatter diagram that appeared on an area seen by several sensors and of correcting the zoom effect that necessarily appears as a result of the varying position of the object with respect to all the sensors.

The calculation of the third dimension being based on the search for similar dots, which is facilitated by the predefined positioning of the sensors, but particularly difficult for uniform surfaces as the tooth surfaces, is associated with these three sensors of the LEDs in the white range in order to reveal the actual color of the object being measured. The image dots thus contain two additional pieces of information, the time (time of the taking of pictures, which will become common for the three pictures, in order to simplify the calculations) and, without this being mandatory, a fifth dimension that is in turn divisible into a chromatic system, and which corresponds to the color information.

Advantageously, these LEDs can also be of a predetermined wavelength (of a few nanometers) permitting to highlight natural markings (groove bottoms or color areas differentiating tumors, gums or shades of the teeth) or markings made before taking the imprint, made with markers of a complementary color.

Advantageously, these markings may be objects of different shapes placed (in the area being measured), glued or accommodated (in the interdental spaces or on the implant heads) on the object being analyzed.

Advantageously, this or these LEDs are placed around each image-focusing lens placed in front the sensor.

Advantageously, these LEDs can be an association between the white LEDs of a predetermined wavelength.

According to a third embodiment, the sensors are distributed over the whole or part of a dental arch, in order to make one imprint in one single exposure, avoiding the clinical scanning of the patient's arcade by the operator. They are thus arranged in a sort of optical-imprint tray permitting to capture the complete arch in one single exposure. This configuration is permitted by the simplicity of the device according to the invention.

The LEDs are distributed along the imprint tray and are controlled together or specifically depending on the analysis being performed and as defined in the first embodiment.

Since the mouth has varying openings, it is possible that the size of the analyzing head of the above-mentioned unit does not allow its introduction as far as the deep interdental areas (molar areas). Therefore and preferably, the present invention provides, according to a fourth embodiment, a variant comprised of endoscopes that are only image ducts, unlike the other dental systems, the head lens of which is in the same position as the sensors described above. In this case l' image is:

either reflected by a mirror or a prism that returns the image of the area being measured to the sensor, which may in turn include a lens system such that the image focal plane is in the plane occupied by the sensor.

or conveyed by an "image" optic fiber reducing and simplifying the optical mounting of the endoscope.

In both cases, the LEDs may be located in the body of the camera and the light is then conveyed through an optic fiber, or they are placed around the front lens, at the end of the endoscope.

Advantageously, these endoscopes can be in a number greater than the number of sensors. In this case, one and the same sensor may be located in front of several endoscopes viewing different areas of the human body being analyzed. This has the advantage of reducing the electronic part of the camera and/or of increasing the amount of image dots during the exposure.

In order to preserve the quality of each image, it is possible to:
  either shift the time, for example by a few 1000ths of a second, of the reading of the image by each endoscope, using a mechanical or electronic shutter.
  or operate with different frequencies, modulations or image intensities, thus avoiding a shift between each of the pictures specific to each one of the endoscopes involved by one sensor.

Finally, and without this being restrictive, there is a particular variant to all embodiments, which uses a micro-mirror of the type "Discovery DMD micro-mirror" from Texas Instruments™, which, associated with the ODLP card, permits to direct the images according to a predetermined angle. This technology, widely used in the projections of the miniaturized video projectors, is used in the present invention as image sensors at different angles.

Thus, according to a sixth embodiment, the device according to the invention includes such a micro-mirror associated with several CCD or CMOS sensors and with the LEDs.

This micro-mirror permits several exposures, at different angles, and at extremely high speeds, without moving the camera. The micro-mirror, placed behind the focusing optics, reflects the image on the whole or part of the CCD or CMOS sensor, by following a simple and direct optical image path. The first image is thus reflected at a predetermined angle. Immediately after, the micro-mirror changes its angle and reflects a new, slightly offset image from an angle different from the first image on the same CCD or CMOS, after resetting, or under another portion of the same CCD or also on a new CCD or CMOS positioned depending on the angles predetermined by the angular position of the micro-mirror.

It is possible to repeat these operations a large number of times simply by varying the angular position of the micro-mirror. This arrangement has the advantage of permitting to use one single optical system on the camera head, one single mirror providing different angles of image reflection, and whereby eventually one single sensor, whether or not located in front of an image-conveying system can be a fiber or a system of lenses.

It is obvious that the more images there are at different angles, the more the measurement is accurate. This is the reason why the present invention is not limited to the use of one single micro-mirror, but eventually to several ones, which has the advantage of multiplying the number of pictures. Thus, when the system contains three sensors, as defined in the first embodiment, and when four viewing angles of the micro-mirrors are chosen (90°, 92°, 94° and 96°), twelve different pictures at different viewing angles are obtained within a few milliseconds.

Thus, the present invention can be defined as being a device for taking dental pictures in three dimensions without using the projection of structured light, unlike with all the existing systems, and comprised of one or several optical systems for focusing one or several pictures, directly associated with several CCD or CMOS sensors, or eventually indirectly, in order to limit the size of the camera head, through a prism, mirror or micro-mirrors endoscopic image-conveyers through lenses or fibers, in a lighting with white LEDs and/or defined chromatic values.

There is of course also the mathematical approach of what is called the small b/h, i.e. the measuring of the third dimension z, since x and y are defined by their position on the pixels of the sensors, when the space between the two optical centers of the focusing lenses are small compared to the distance h of the field depth at the optical center of the lenses.

The model used for a small b/h is:

$$|\text{right}(x) = \lambda(x) \cdot |\text{left}(x + £(x))$$

where £ is the geometric deformation.

$$\partial z = a£/b/h$$

the Shannon principle is used based thereon to solve the problems of disparity of the measurements due to sub-pixelation.

$$px_0(\mu m) = \frac{\varphi \cdot x0}{\|u(\cdot + \mu m)\| \varphi_{x0} \cdot \|\breve{u}\| \varphi_{x0}} \int u(x + \mu m) \cdot u(x) \cdot dx$$

$$\text{where } \breve{u} = \int px_0(x) \cdot u^2(x) \cdot dx$$

The advantages and features of the device according to the invention will become clear from the following description, which relates to the attached drawing, which represents several non-restrictive embodiments of same.

BRIEF DESCRIPTION OF THE DRAWINGS

FIGS. 3a, 3b, 3c, 3d and 3e show cross-sectional views of the same portion, according to different embodiments.

FIGS. 4a, 4b and 4c show views of different configurations of the device according to the invention used in dentistry.

FIGS. 5a, 5b and 5c show schematic views of details of FIGS. 4a, 4b and 4c.

DETAILED DESCRIPTION OF THE DRAWINGS

Figure 1:
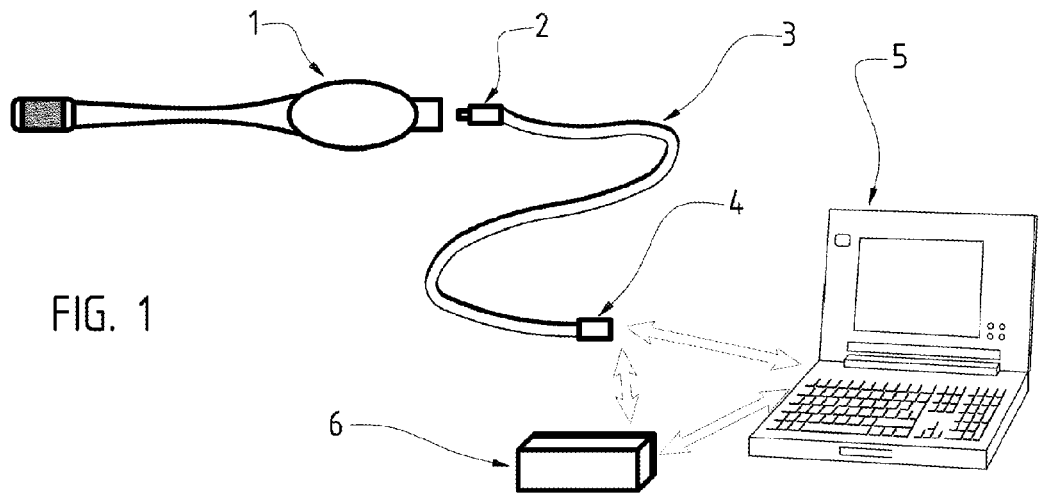
FIG. 1 is a schematic, perspective and exploded view of the device for taking three-dimensional and temporal measurements according to the invention.

As shown in FIG. 1, the device according to the invention comprises a camera with fixed focal length 1 using the technology described in the invention, a connection 2 between the camera 1 and a cable 3 serving as a data supply and transfer, a connection 4 between the cable 3 and a computer 5, of the USB type, and a housing 6, which can be placed as an intermediate device for the adjunction of a driving card for the processor of the camera and/or image processing when the latter are not placed in the camera or in the computer.

This same camera 1 can use a wireless WiFi connection for the transmission of images, or data from the images, and a charging system for rechargeable batteries for the energy to supply to the camera.

To detail each part of this invention, we will refer to FIGS. 2a, 2b, 2c, 2d and 2e, which show a dental clinic option in its functional aspect.

The device shown in these figures includes a dimensional color measuring camera, including the total capturing of one or several pictures of the object being measured, with a fixed, stable, pre-calibrated and motionless focusing system, without any dynamic correction of the focusing or without projection of structured light projected or scanning the object being measured, of the type dots, lines, grids at known fixed or shifted pitches, having lighting LEDs of white light or known and previously defined wavelengths permitting to highlight the colors one wants to extract from the image being measured. The sensors, which are themselves in a fixed, stable, pre-calibrated and motionless position, are placed behind the optical system, here two in total, in order to observe the whole of the object being measured from a different angle previously defined at the time of calibrating the camera during manufacture. Unlike all existing systems, this camera does not include any division of the captured image, any mechanical focusing movement and any projection of structured light. The judicious combination of the de-located lights, i.e. those that illuminate only the scene, permits to highlight the elements of interest for the observer and the analyses he wants to perform in terms of measuring or diagnosis.

These features are considered fixed and not changeable by the operator, except the selected type of lighting, although this function can be controlled by a series of automatic actions leading to the desired diagnosis. To this end, the operator (dentist or dental technician) has a computer indicating the operations the camera can perform and permitting him to make the choice between one function and another.

Thus, in the "measuring" function, after having selected this mode of action, the operator will launch the measuring using a button located on the camera, or a pedal connected to the computer or intermediate housing, after having positioned the camera on the area to be measured, and will stop it when he will consider he has enough information, he will stop pressing or will press a second time. Having a colored image allows the operator to have an automatic analysis of (usually white) dental and (usually red) gingival areas, which is impossible with the current methods using structured light projections. Likewise, by positioning indices of known colors, he has the possibility of making discriminative analyses for identifying objects in the image, but also their position (implant or pin heads, orthodontic brackets . . . ) or also to facilitate the correlation of the pictures (marks, colored lines on the object or selective color as groove bottoms, . . . ).

Thus, in the diagnostic function he will select on the computer the desired type of diagnosis, e.g. melanoma, and the camera will start a scanning of the wavelength corresponding to the highlighting of the areas of interest for the preselected wavelengths and present in a 3D image. In addition, thanks to the 3D analysis of the object, the recovery of the measurements over time will permit to better monitor the evolution of said pathology. It is indeed admitted by the professionals that the study of a suspicious image can be done in 2D, but that mainly the evolution of its volume and its color serves as a reference for monitoring his dangerousness over time. Having a volume referred to a mathematical center (such as e.g. the barye center) permits to superimpose the images on a center depending on the object and not on the observer, in order to objectively assess the evolution of the volume, the analysis of the color being reported on a 3D shape, which is not the case today with the methods performed on 2D surfaces or those using lights or the structured waves (OCT, scanner or MRI).

Thus, in the color analysis function, after having selected this function, the color analysis of the volume measured and reported on it can be done on bases that do not depend on the metameric match that depends on the lighting present in the room of the operator. Having several wavelengths will permit to approximate a continuous spectrum and to have a spectro-colorimetric analysis. In order to simplify this operation, it is possible to refer only to the three complementary RGB colors and to carry out a simple colorimetric analysis.

Finally, and this is not restrictive, having two 2D images to form a 3D image permits, in real time, to switch the vision without changing the camera to 2D pictures in color like with all the cameras nowadays available on the market for dentistry. Since it does not use structured light projection, this camera thus permits to perform all the functions known today, including the zoom effects, but also diagnosis applications in color on 2D images such as the detections of caries by fluorescence in the green, blue or ultra-violet ranges (500 to 300 nm) or visual displays in the red and infrared radiation (600 to 900 nm), depending on the LEDs that will have been emulated in the analysis.

This same zoom effect in color image or the emulations can be performed on the 3D images. It is obvious that the transition from color to grayscale will only be an offset function that will be present in the software controlling the image processing operations resulting from the operation of the camera.

The connection between the camera and the computer can be a wired or wireless one.

According to the invention, the wired connection 3 will preferably be by means of a self-powered USB connection 4 with a specific port 2 on the camera side 1. This specific connection 2 will be designed so that it is adaptable to all forms of cameras, which, as will be seen below, can adopt various forms.

Likewise and according to the invention, the connection can be wireless, for example in Wifi mode, and this is not restrictive. In this case, the antenna will be included in the camera or connected at the location of the specific connection 2. Likewise, on the computer will be inserted, in the USB connection, an antenna for sending and receiving data corresponding to the orders given by the program located in the camera or in the computer. This will allow fast, friendly and easy communication, irrespective of the configurations of the medical, dental offices or dental prosthesis laboratories.

According to the invention, the computer 5 is a standard one with an included or separate screen. This computer uses standard cards especially programmed to control the camera or specific control cards that are placed on the bus.

In the event the computer could not be equipped or is previously present in the care unit, an intermediate casing 6 is positioned between the camera and the computer, in order to compensate for this lack. Likewise and for the same function, this casing will be positioned downstream of the computer and the USB connection 4 of the connection will be plugged directly into the USB port of the computer without any intermediate device.

Figure 2A:
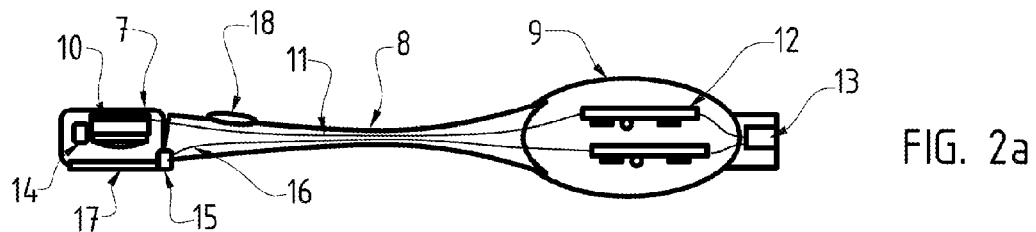
FIGS. 2a, 2b, 2c, 2d and 2e show schematic views in longitudinal cross-section of part of the same device, according to different embodiments.

In the configuration shown in FIG. 2a, a segment has the head 7 of the camera 1, an arm 8 permitting its insertion into the mouth and a body 9, often outside the mouth. The head has the segment of the optical unit of a central lens 10 of the optical system comprising three units (fixed focusing lenses, i.e. without adjustment of the focusing before exposure, and CCD or CMOS sensors) connected to the image connection card 12 by means of a preferably shielded cable 11, in order to prevent any interferences harmful to the quality of the information being transmitted. This card is in turn connected to the computer 5 or the specific casing 6 through the specific connector 13 belonging to the camera 1. This same longitudinal segment permits to distinguish the LEDs placed towards the optical system 14 within the head protected by the protective glass and/or at the periphery of the optical system, outside the latter 15. A button 18 permits to activate the exposure, when the pedal is not used. Using a delay-free system for taking pictures permits to take this 3D image by means of the button without risking the blur that can be created by an involuntary movement.

The design of this camera is intended to cover a relatively narrow field of reading (a volume of 15×15×15 cm) with an accuracy within a few microns. To this end, the fields scanned by the viewing systems are identical, but the picture dots have a slightly different angle.

Figure 2B:
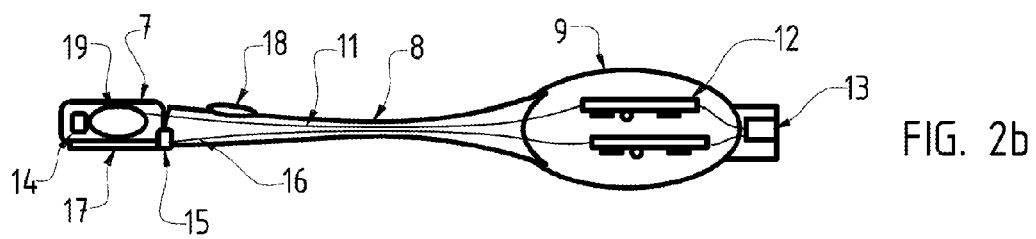

In the configuration shown in FIG. 2b, we see a longitudinal cross-section with only two optical systems, of which can be seen here only the cross-section of one of the two systems 19 and the LEDs 14 and 15, which can occupy the same positions as those described above. This configuration permits to significantly reduce the volume of the camera head, but requires a more substantial software development.

Figure 2C:
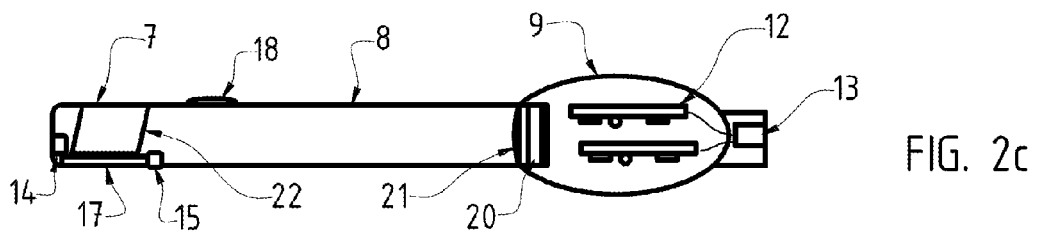

In the configuration shown in FIG. 2c, the CCDs or CMOS sensors 20, and the fixed focusing systems 21, which are here placed in the body of the camera, are positioned in front of image-reflecting mirrors. These mirrors, which may be two or more in total, part of one of them 22 can be seen, have an angular position such that they can cover the same reading area according to slightly different angles permitting the sensor to record the same scene with a slight spatial offset.

Figure 2D:
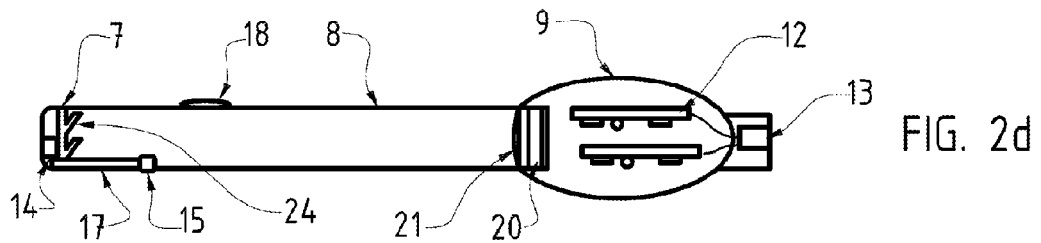

In the configuration shown in FIG. 2d, the CCDs or CMOS sensors 20 and the fixed focusing systems 21 are still placed in the body of the camera, but the mirrors are positioned in front of micro-mirrors 24 controlled by the processor card, e.g. of the FPGA type, located in the camera 1, in the computer 5 or in the intermediate casing 6. It is known that the micro-mirrors, which are widely used for projecting images in the video projectors, are rarely used in the viewing techniques. These micro-mirrors can be oriented in the three spatial directions, this very quickly, one single mirror can replace a dozen mirrors, and even more, which permits to see a slightly different scene, a common portion of which will be according to common angles. The DMMD (or Digital Micro Mirror Device), also referred to as DLP (Digital Light Processing), e.g. from Texas Instrument, use micro-mirrors (e.g. 10 μm×10 μm), the angle of which changes quickly under the action of the voltage variation or the voltage. Since their number is larger than 1024×1280, the announced accuracy is possible. The voltage of the angle change is sent to the electrodes indicating the torsion to be applied to the knee-joint bearing and orienting the mirror. A polarity reversal is sufficient to put the mirror in another position. The mirrors are so small that the change occurs within less than 15 μs.

This solution is particularly interesting because it permits to sectorize the pictures and to record them, thus facilitating the correlations of the images during the image-processing phase.

It is obvious that the same configuration can be designed, according to the invention, with the sensor located in the head or the arm of the camera, thus avoiding a loss of the image or a too large arm that could hinder the insertions into narrow areas. Likewise, one single sensor can be sectorized at the surface so that it is capable of receiving several pictures at the same time.

Figure 2E:
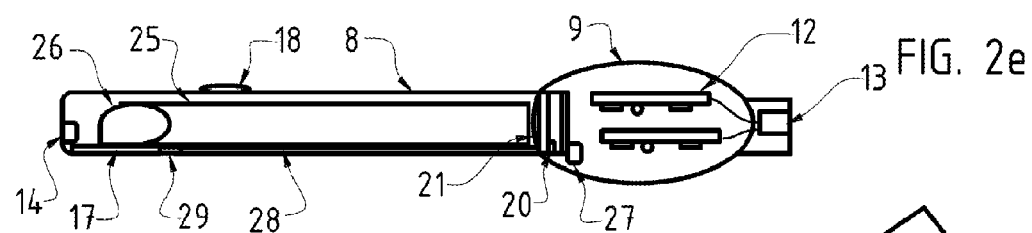
Figure 2F:
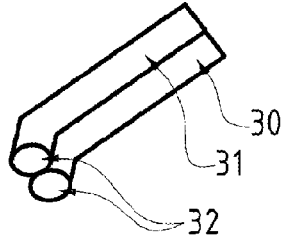
FIG. 2f shows a schematic perspective view of a portion of FIG. 2e.

Finally, in the configuration shown in FIG. 2e, the CCD or CMOS sensors 20 and their optical system 21 placed in the body of the camera are positioned in front of image-transmitting optical fibers 26, the orientation of the output segment of which or the torsion applied to the end, visible in FIGS. 2f, 30 and 31, permits to cover an identical field according to different angles 32. These fibers can be in a multiple number, thus permitting a capturing according to several angles, and the optical systems and sensors can be positioned in the head or the handle, in order to avoid reductions in signal image.

It should be noted that for all the configurations shown in these figures the LEDs can be positioned in the head of the camera 14 or in the body of the latter 27. In the latter case, they are placed in front of a light-transmitting fiber of 28 having its light-projecting end located in the head of the camera 29.

Figure 3A:
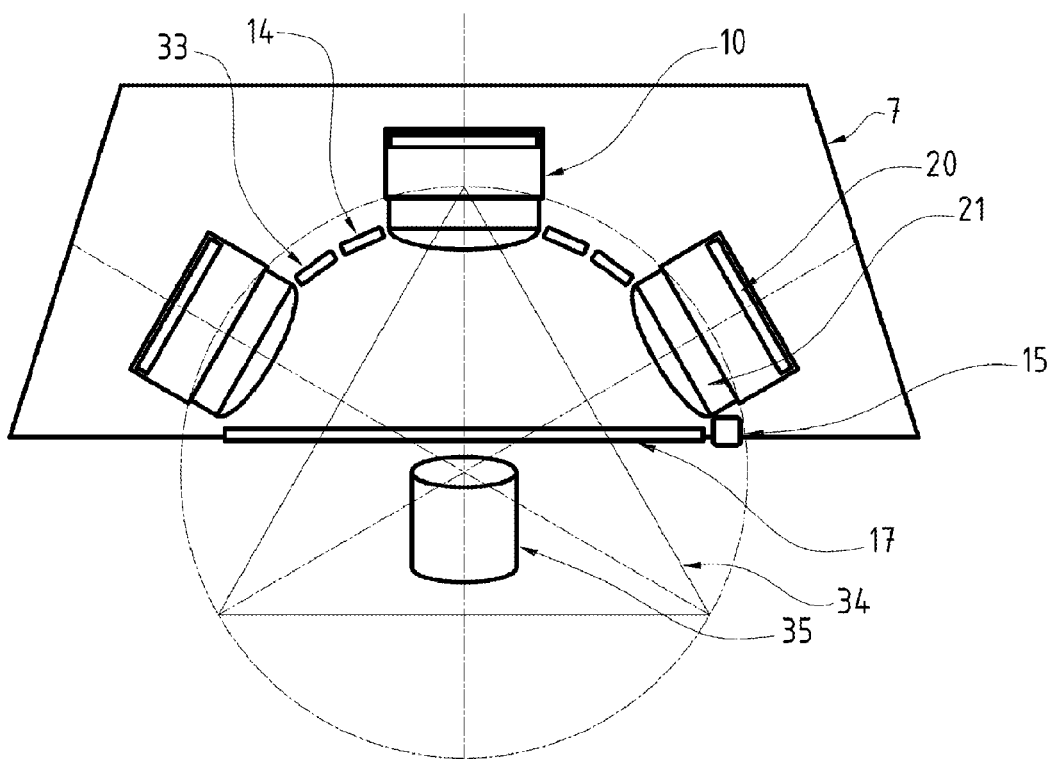

When referring now to FIG. 3a, we can see a representation of the device according to the invention using in the camera head 7 three fixed 10 and equilateral 34 optical systems for focusing the image 21 positioned around the object being measured 35 and placed at a fixed and predetermined distance by calibration before the CCD or CMOS sensors 20 placed at the end of the casing, without using endoscopes or reflecting mirrors and according to the three-sensors configuration, showing the possible position of the LEDs for specific lighting 14 or with light of specific wavelengths 33. As can be seen in this segment, these same LEDs 15 can also be placed around the window 17, which allows to better illuminate the scene being measured.

Figure 3B:
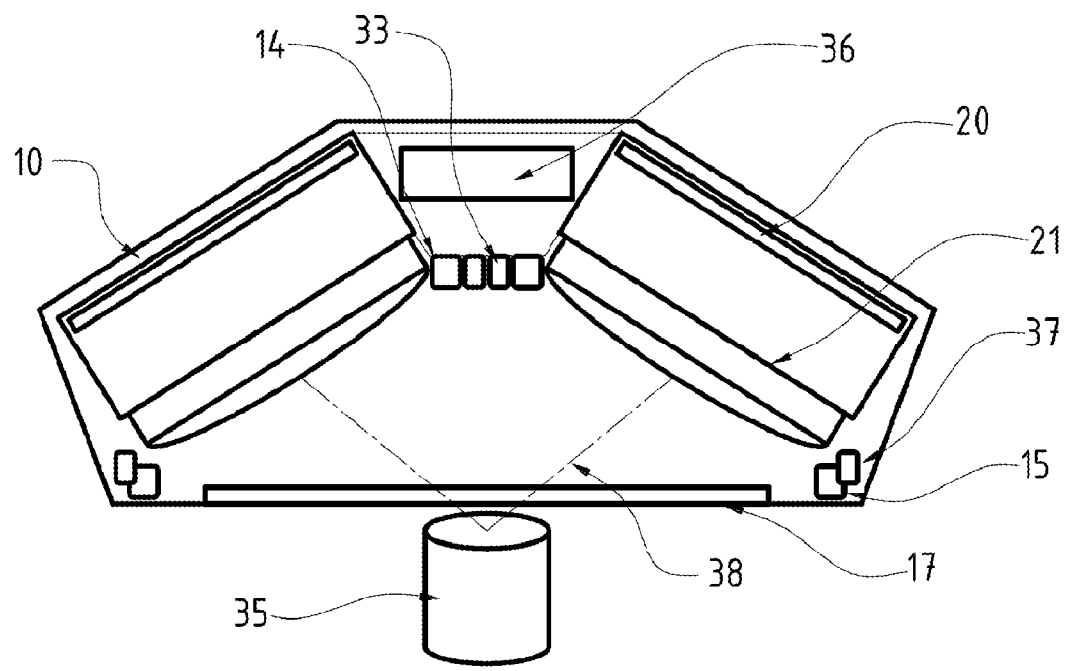

When referring now to FIG. 3b, we can see a frontal cross-section of the configuration of FIG. 2b; the two fixed optical systems for focusing the image 21 are positioned around the object being measured and placed at a fixed and predetermined distance by calibration before the CCD or CMOS sensors 20 placed at the end of the casing, without using endoscopes or reflecting mirrors. We find the LEDs themselves in a central position both for the LEDs with white light 14 and for the LEDs with specific wavelengths 33. These LEDs 15 and 37 can also be placed around the glass protecting the optical unit 17. The position here is in the particular form of an isosceles triangle 38, but this is not restrictive. Any positions of the optical systems 10 can be contemplated, as far as the configuration is fixed in the measuring and picture correlation software. In this same figure, because of the reduction in volume of the optical elements, an image processing system 36 (image processing) can be placed proximate the sensors, which prevents the losses of information along the connection wires.

Figure 3C:
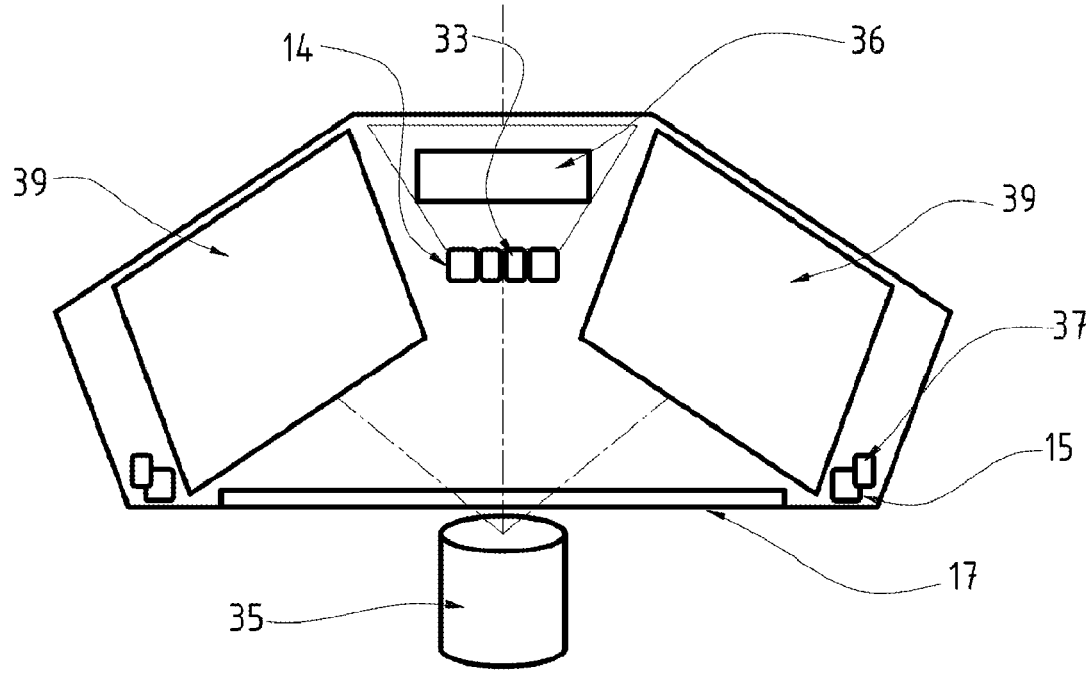

When referring now to FIG. 3c, we can see that the image reflecting mirrors 39, which may be two or more in number, are positioned in the head of the camera according to different angles and permit capturing the image on one or several CCD or CMOS sensors 20 placed behind the focusing systems 21 in the body of the camera 1, which are in turn positioned in front of the image-conveying mirrors involved. We find here the various LEDs 14-17-33 and 37 as well as eventually the image processing system 36.

A variant is provided in FIG. 3d. In this case, only one mirror 40 is used and the optical systems 10 including the focusing systems 21 and the sensors 20 are arranged according to a slight angle. This very special arrangement can be seen in the complementary drawing, in which can be seen, through the protective glass, the only mirror 40 located in the head of the camera and the position of the two sensors 42 including a relatively small angle, of a few degrees, so that the mirror surface is necessary and sufficient to reflect an image according to the two different angles corresponding to the position of the two sensors.

Obviously and according to the invention, this arrangement is a particular case and it can be comprised of more than one mirror and more than two sensors.

When referring now to FIG. 3e, corresponding to the configuration of FIG. 2d, we see the micro-mirrors 43 arranged at the place of the single static mirror 40. We could use several DMMD components, but one is enough. The multiplication permits to multiply the images and to increase the measurement accuracy while simplifying the algorithms for searching the third dimension.

In this arrangement, one single unit comprised of a focusing system 21 and CCD or CMOS 20, without this being restrictive, is located in the body of the camera 44 or in a position directly near the micro-mirrors in the head of the camera 45.

In the arrangements described in FIGS. 3c and 3e, we can also convey the image using image-transmitting optical fibers, as shown in the configuration of FIG. 2e. In this case, one or several optical fibers are placed in front of the mirrors, the micro-mirrors or directly towards the object being measured (FIG. 2f), eventually behind an optical system and on the axis of the CCD or CMOS sensor or sensors placed in the body of the camera, which are in turn positioned in front of the other end of the image-transmitting optical fibers. It is also possible to use very short fibers and to place the optical systems+sensor 10 in the head of the camera, which significantly limits the mounting and the adjustment of the system.

Figure 4A:
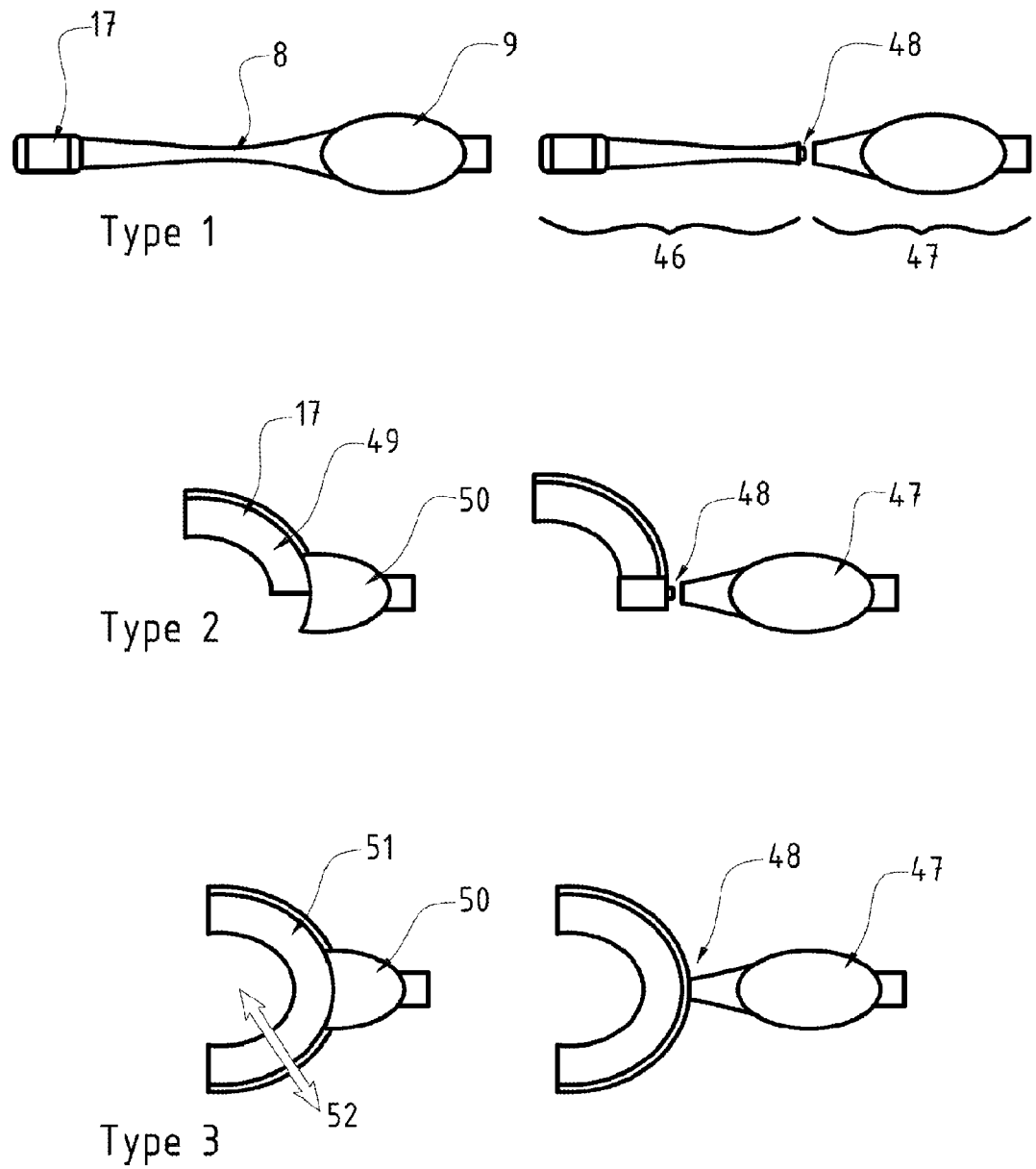

FIGS. 4a, 4b and 4c show how the present invention meets clinical needs that were so far unanswered in dentistry and ophthalmology.

In dentistry, the practitioner, who wants to make a diagnosis or an imprint in order to make a prosthesis or implant needs two types of approach, a fast one that provides him only the necessary information (in terms of measured area and accuracy offered) and the other one complete and accurate. For example, making a crown on a mandibular molar can be done by dental CADCAM when the optical imprint of the preparation area is accurate, complete and neat, when the optical imprint of the antagonist teeth provides at least the measurements of the points of contact (cusps, grooves) and of the shapes of the arches, which does not require the same attention. Likewise, an imprint for a teeth-straightening apparatus (orthodontics) will not require as much precision as for making a ceramic bridge on heads of implants.

That is why the inventive device is available in three types of dental cameras.

Type 1, schematically shown in FIG. 4a, represents the device of the invention in dentistry permitting to take several pictures, but requiring the displacement of the measuring head. This is a camera that takes a picture in 3D and in color of the dental arches using the principle of the invention, i.e, without modification or adjustment of the focal length and without using structured light, but using the projection of LED lights in order to promote the identification of the tissues and pathologies. It can be of one single part or be divided into two parts, one referred to as "measuring head" 46 and including the optical system (lenses+CCD or CMOS sensors) associated with the LEDs, and a second part 47 referred to as "processing body" containing the control and image-processing cards, eventually available for other forms of "optical imprint head" connectable to a specific plug 48 that gathers on a universal body 47 several types of "imprint heads", such as the camera head 46.

Type 2 is formed of the same arrangement of basic units, present in the head of the camera, but multiplied and distributed in a sort of optical imprint tray 49 for a half-arch. This arrangement is made possible because, by having only one image conveyer, without conduit for structured light, we can multiply along the half-arch, behind the protective glass 17, the arrangement located at the end of the camera and thus not be required to go through the arch for obtaining the information. One single picture permits to capture the entire tooth surface located on the axis of exposure, not including the taking-off areas. This taking of pictures is fast and sufficient to have a measurement or a complete information, without causing pain to the patient.

The image-processing part can be incorporated into the imprint tray 50, or the latter can be disconnected after an exposure 48 similar to that of type 1, which allows this tray to be inexpensive, simpler and to use the same "processing body" containing the control and image-processing cards 47 as type 1.

The connection can be made through an additional cable or a wireless system, e.g. Wi-Fi, uniting the connector 48 and the camera casing 47, not shown in the drawing, in order to facilitate the manipulation of the small reading and imprint-taking system.

Type 3 is an extension of type 2 for the whole arch, having a protective glass having the shape of the complete arch 51, protecting the optical systems pre-positioned as in the system of FIGS. 2a and 2b.

Like type 2, it is made of one single part with an image-processing system located in the handle 50 or can be disconnected thanks to a specific plug 48 allowing it to take advantage of the interchangeable image-processing system 47.

This type 3 will be very useful for large occlusal reconstructions corresponding to a prosthesis on the opposite arch or for determined diagnoses that do not require a view of the taking-off areas. It will also find a major application by being used advantageously for the correlation of the radiological or cone beam pictures and will thus facilitate the collection of information from the optical imprint and the radiation imprint. Very important technique and demand in the field of the implantology, this type 3 will greatly simplify the process and ensure the long-awaited link between the clinical X-rays and the dental technician's exercise in the CADCAM in his laboratory.

We know indeed that in the radiological imprint in 2D scanner or cone beam, or 3D MRI the information of the outer surface of the gum and the teeth exists, but is not accurate. The knowledge of this same surface using the optical imprint resulting from our invention permits to combine the two files, in order to have a complete, consistent and accurate aggregate permitting to make implants safely and to use the existing dental CADCAM software.

A segment 52 of FIG. 4a, type 2 or 3, permits to see two variants of the arrangement described in FIGS. 3a and 3b. It is increasingly possible to reduce the volume of the optical systems by associating sensors and focusing lenses, as shown by the webcams included in the screens of the laptops. Since our focusing system is fixed and accurate in relation to a defined volume and field depth, we thus propose, according to the invention, to miniaturize and multiply the sensors, in order to benefit from an analysis of the entire area being studied, the taking-off included, by distributing these units along the optical imprint to be made.

FIG. 4b thus represents a variant of these type 1, 2 and 3 systems with miniaturized reading heads (focusing lenses and sensors) 53 surrounded by LEDs not visible in the drawing and protected by a glass 17. This variant covers the whole or part of the arch, and permits to take pictures of the labial 54, occlusal 55 and lingual 56 surfaces in one single exposure. This is thus a special, more complete, more voluminous camera, but capable to take a complete and accurate picture of the areas with and without taking-off. It can be used according to a configuration of the type 1 localized to an arch area, the type 2 for a half-arch or the type 3 for the complete arch. The taking of pictures is complete, total and very fast. The correlations and measurements are facilitated by a priori knowledge of the image-processing algorithms, the arrangement and the fixed position of the optical systems and the focusing systems, object of the invention. This 4b type is an arrangement usable in the mouth, but it will find its full application especially in its application on working models made of plaster, in dental offices and laboratories. The taking of an imprint is referred to as a centrifugal optical imprint, because it converges toward the center of the image.

FIG. 4c shows another convex-shaped variant for taking an imprint in the traditional imprint trays 57, thus avoiding that the dentist has to perform the casting of his model, but allowing him to make a traditional imprint, if he prefers so, and to transmit it to the laboratory in a digital form (solid medium or internet). The taking of an imprint is referred to as a centripetal optical imprint, because it converges toward the outside of the image.

FIGS. 5a, 5b and 5c represent detailed views of the optical window of the viewing system in dentistry for a camera with two optical systems 64 in FIG. 5a, with three optical systems 65 in FIG. 5b, and for a half-arch in FIG. 5c. In these figures is shown a positioning mode, but this is only an example, by detailing them we can see the position of the image conveyers 58, which may be lenses or mirrors and the possible position of the "white" LEDs 59 and of the LEDs of specific wavelengths, such as for example, and this is not restrictive, of the LEDs in the red and/or infrared range 60, in the orange range 61, in the green range 62, in the blue and/or ultraviolet range 63.

As can be seen in FIG. 5b, the white LEDs 66 can be positioned at the periphery of the protective window 17.

Each of these LEDs has a specific role that will be described more in detail later in the text. The aim of the so-called "white or daylight" LEDs is to identify the "true" colors perceived by the human eye, accurately promoting the signal-to-noise ratio, while the aim of the LEDs with predetermined wavelength values is to highlight areas of interest at mathematical (correlation areas . . . ), pathologic (pathology reactions, fluorescence . . . ) or anatomical levels (the gum is red and the teeth are white).

Figure 6:
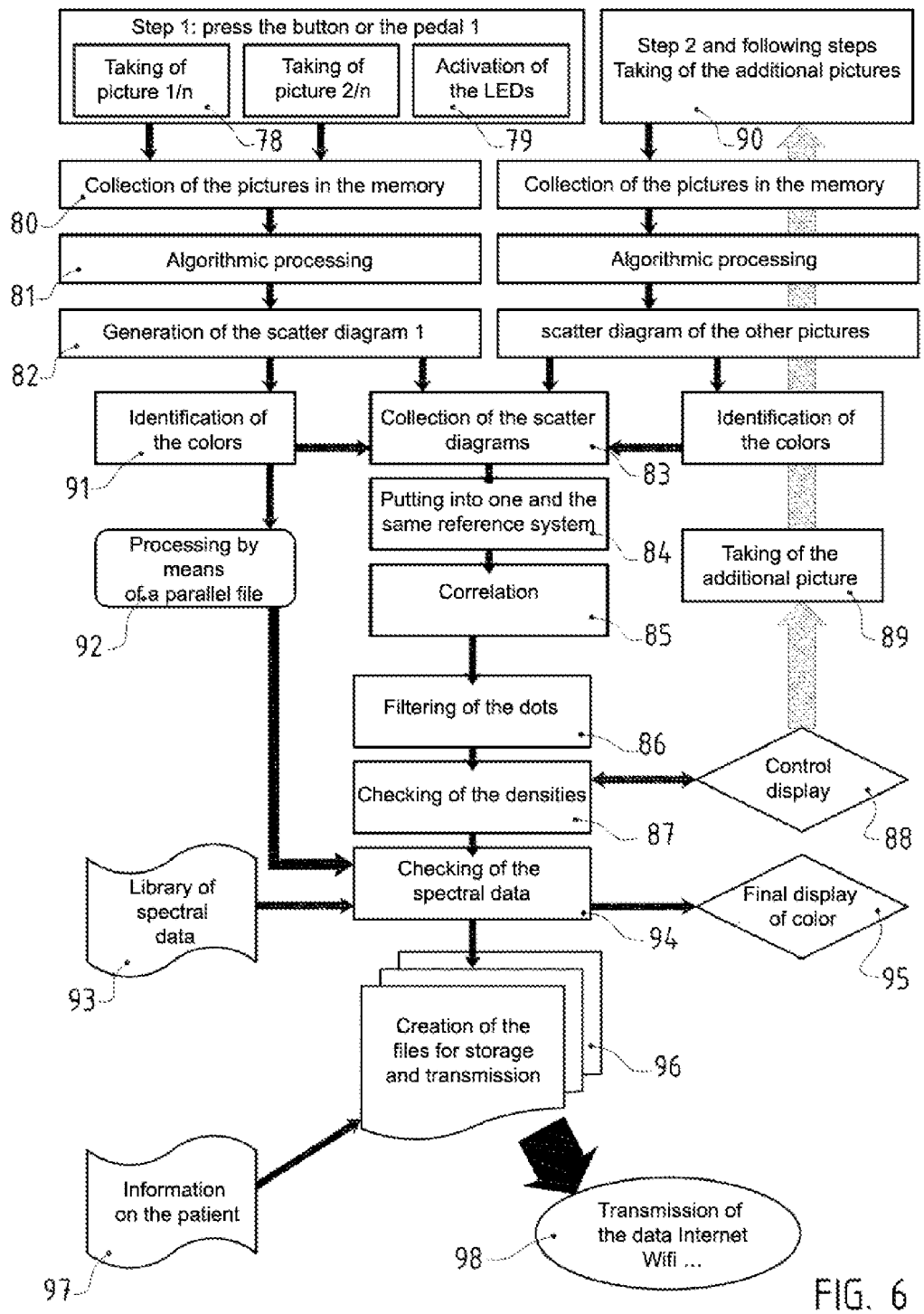
FIG. 6 shows a schematic illustration of the various steps for processing the measurement using the device object matter of the invention.

When referring now to FIG. 6, we can see the different steps of processing of the dental measurement and the tissue analysis using the device object of the invention.

In order for the operation of the device of the present invention in dentistry to be well understood, in this FIG. 6 have been shown the various states of its implementation. We will state, by way of an example, that there may be, and this is not restrictive, additional steps, such as the spectrocolorimetric analysis.

In a first step, the operator, whether he is a dentist working with a chair, an assistant dentist or a lab technician, takes the camera in his hand, which results into emulating the software, thanks to a small ratchet for putting into operation existing on the camera support or included in the camera itself. He inserts into the patient's mouth 78, on the imprint or on the duplicate model of the oral picture, the camera (and displays its position by means of a screen, not visible on the diagram, but corresponding to the screen 5) of FIG. 1, the picture the camera captures). He presses the button 18, starts the reading and the recording of the systems for dynamically capturing pictures, i.e. a film of successive pictures and which will stop only when the button 18 is released or after a second pressing of the button. A simple reading function without recording is possible by a simple selection at the level of the general menu selected when taking in the hand the camera, which asks question 1: "taking an imprint 3", "simple 3D display" or "simple 2D display" at the computer 5.

The imprint will be complemented images after images by the fast resetting of the sensor and the sending of the successive images into the memory 80 of the camera 1 and/or the computer 5 and/or the intermediate casing 6. An algorithmic processing 81 will be performed on each datum, in order to extract the features permitting to know the spatial position and the color of each dot measured in a reference system. This will permit to generate a scatter diagram 82 in this reference system. These scatter diagrams will be collected 83, in order to put them in a common reference system 84, then correlated 85 in one single scatter diagram and of the same reference system. It is obvious that this procedure may be slightly different depending on the type of configuration adopted, as defined in FIGS. 2a to 2e. Since the pictures are very rich in dots, they will be filtered 86, in order to extract from them the necessary and sufficient data and/or to present them in the form of algorithms or simple dot-per-dot matrix values. This will be possible, for example at this level without it being absolutely necessary, because it is possible to perform this step on a video image when taking the image or completely downstream on the logarithmic functions, to check the density of the information based on the surfaces being measured 87. This operation is obviously important because the right choice of an extent of presence of a number of dots per surface unit or the choice of a judicious offset permits to know whether the measure is sufficient to provide an accurate optical imprint. This verification of the data will be done 87 and will lead to either a validation of the imprint or to the taking of additional pictures 89 and 90. This decision can be taken thanks to a presentation on the screen 5 of the areas being measured 88 in red color (for example) for the areas to be complemented and by a displaying in green color (for example) for the areas that are rich enough.

The additional pictures will follow the same path as the initial pictures and will complement, e.g. at 83, the insufficient scatter diagram.

There only remains to collect the validated data 94 of each scatter diagram and to eventually make a final display 95. The whole will lead to the design of a first type of file referred to as "File of taking of optical imprint" 96.

As we said, when taking a picture 78, the lighting with LEDs 79 is activated. In addition to the questions about the choice of the types of pictures, there are three other questions in the menu "optical imprint" or "spectral analysis" or "pathological analysis". This second choice permits to define the type of lighting chosen. If we opt for the optical imprint, the LEDs referred to as "daylight LEDs" 14 or formed of LEDs that through their complementarities provide light of a known spectrum 33 will be activated. The imprint will thus be in color, which will permit to generate the requested information 91. This information will either complement the scatter diagram 83 or fill a specific color file 92 which, compared to the stored files 93, will permit an approximate identification of the hue. If we want to better know the color, we will proceed to a spectral scanning of the IR to UV range by activating the specific and successive LEDs 60-61-62-64 by choosing the "spectral analysis" function. These two files will permit to generate a second specific type of file 96 "colors in three-dimensional pictures" obtained by a spectrocolorimetric analysis. Finally, by activating the "pathological analysis" function, we will activate specifically and/or successively these same LEDs with a penetrating intensity specific to each pathology looked for, which will allow us to generate a third type of file, referred to as "pathological file" 96 with a colored three-dimensional picture showing the detections made.

These files, of the first, second and/or third type, are attached to the pre-established patient's card (97) and transmitted locally (Wifi, USB cables, Ethernet . . . ) or externally (Internet . . . ) in a specific or standard format (STL . . . ).

We see thus that, unlike all known systems, the present invention permits to generate dynamic optical imprint files in color with spectral data corresponding to spectrocolorimetric measurements.

Advantageously, according to the invention, it is possible to follow the movements of the jaw bones by placing the camera in the vestibular area of the jaws of the mouth, red lines, and this is an non-restrictive example, are drawn on the upper jaw bone and the lower jaw bone, then the movements of the two jaw bones are filmed in maxillary view, from the starting point to the end of the movement. The camera takes pictures where a scatter diagram moves (the lower jaw bone) with respect to the other scatter diagram (the upper jaw bone, in principle considered as immobile). Since the marking belongs, independently, to each of the jaw bones, the system will follow only the movement of colored markings highlighted at the time of lighting of the red LED. Since the same marking exists at the time of the optical imprint made separately of the upper jaw bone and the lower jaw bone, the correlation software will use this colored marking not only to correlate the images of each jaw, but also to display the movements according to the fourth dimension, the time.

Advantageously, and this is a very interesting feature of the invention, it is possible to work in 2D color starting from 3D pictures. This can be done in two different ways:

Since we use a daylight 79, without projection of frames or other structured lights, the display 5 in our control process during the taking of pictures 78 permits us to use this optical imprint camera as a simple 2D camera considerably limiting the investment cost for the practitioners.

We can also perform this 2D display after digital processing and highlighting of the highlighted pathological areas by scanning with the LEDs of specific wavelengths. This technique is obviously possible only starting from 3D images.

I claim:

1. A three-dimensional and temporal measuring device through optical color imprint usable in the dental field, wherein the device for taking three-dimensional dental pictures does not use structured light projection, the device comprising:

a stereo camera comprised of at least two CCD or CMOS color sensors in a predetermined position defining, because of resetting speed, the reading speed, thus the speed of taking successive imprints, and permitting a static or dynamic reading;

an optical system of fixed and preset focal length permitting to transmit to the sensors, without distortion, data displayed on the operating field;

an LED lighting system for illuminating the area of taking an imprint; and an electronic system located behind or proximate each of the sensors, ensuring control thereof control of LEDs illuminating the area of taking an imprint, wherein said electronic system comprises:

a central control unit capable of collecting, storing and organizing the data captured by said sensors; and a card for controlling said LEDs, depending on said central unit, wherein said sensors are distributed over a whole or part of a dental arch in order to make an imprint in one single exposure, avoiding clinical scanning of the arch, said sensors being arranged in an optical imprint tray permitting to capture the complete arch in one single exposure.

2. Device according to claim 1, wherein said LEDs are distributed along the imprint tray and are controlled together or specifically depending on the analysis being performed.

3. Device according to claim 1, wherein the electronic system further comprises:
a standard supply card capable of operating on USB or on battery; and
a miniaturized memory card in the camera, permitting to store the pictures and to transfer said pictures to the computer.

4. Device according to claim 1, further comprising three sensors intended to be positioned uniformly, according to a known geometry, around the object to be studied, fixed focusing lenses positioned in front of each sensor according to a central optical axis, the position and the spatial orientation with respect to each other of which are perfectly known, said lenses in co-linear position with respect to the viewing axis of the sensor forming three image paths, one for each sensor.

5. Device according to claim 1, further comprising:
two sensors positioned uniformly around the object being studied, in a known geometry, and focusing lenses placed in front of each sensor according to a central optical axis, the position and spatial orientation with respect to each other of which are perfectly known, said lenses, in a position co-linear with respect to the viewing axis of the sensor, forming two image paths, one for each sensor.

6. Device according to claim 4, wherein the LEDs are of a predetermined wavelength permitting to highlight natural markings or markings made before taking the imprint, made using markers of complementary color.

7. Device according to claim 4, wherein said LEDs are placed around each image-focusing lens placed in front of the sensor.

8. Device according to claim 4, wherein the LEDs are comprised of an association of white LEDs and LEDs of a predetermined wavelength, so that the measurements are made from natural colors, and not from artificial colors.

9. Device according to claim 1, further comprising a micro-mirror associated with the sensors and the LEDs.

10. Device according to claim 1, wherein the optical system comprises at least one endoscope.

* * * * *